(12) United States Patent
Dickerson

(10) Patent No.: US 7,913,497 B2
(45) Date of Patent: Mar. 29, 2011

(54) DESICCANT CARTRIDGE

(75) Inventor: Brian E. Dickerson, Littleton, CO (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/884,318

(22) Filed: Jul. 1, 2004

(65) Prior Publication Data

US 2006/0000223 A1 Jan. 5, 2006

(51) Int. Cl.
*F25D 17/06* (2006.01)
(52) U.S. Cl. .................. 62/94; 62/606; 62/617
(58) Field of Classification Search ............... 62/92, 93, 62/94, 614–617, 606, 640, 654; 220/87.1; 55/275, 387
See application file for complete search history.

(56) References Cited

U.S. PATENT DOCUMENTS

| | | | |
|---|---|---|---|
| 2,909,903 A | 10/1959 | Zimmermann | |
| 2,951,348 A | 9/1960 | Loveday et al. | |
| 2,964,918 A | 12/1960 | Hansen et al. | |
| 3,199,303 A | 8/1965 | Haumann et al. | |
| 3,797,262 A | 3/1974 | Eigenbrod | |
| 3,941,124 A | 3/1976 | Rodewald et al. | |
| 3,946,572 A | 3/1976 | Bragg | |
| 4,015,959 A * | 4/1977 | Grote | 96/136 |
| 4,018,582 A | 4/1977 | Hinds et al. | |
| 4,211,086 A | 7/1980 | Leonard et al. | |
| 4,216,819 A | 8/1980 | Notaro | |
| 4,253,519 A | 3/1981 | Kun et al. | |
| 4,279,127 A | 7/1981 | Longsworth | |
| 4,388,086 A * | 6/1983 | Bauer et al. | 95/118 |
| 4,388,809 A | 6/1983 | Sarcia | |
| 4,510,760 A | 4/1985 | Wieland | |
| 4,529,411 A | 7/1985 | Goddin, Jr. et al. | |
| 4,542,010 A | 9/1985 | Roman et al. | |
| 4,561,287 A * | 12/1985 | Rowland | 95/11 |
| 4,570,819 A | 2/1986 | Perkins et al. | |
| 4,575,386 A | 3/1986 | Hamers | |
| 4,581,047 A * | 4/1986 | Larsson | 96/131 |
| 4,591,365 A | 5/1986 | Burr | |
| 4,627,860 A | 12/1986 | Rowland | |
| 4,701,187 A | 10/1987 | Choe et al. | |
| 4,826,510 A | 5/1989 | McCombs | |
| 4,841,732 A | 6/1989 | Sarcia | |
| 4,870,960 A | 10/1989 | Hradek | |
| 4,971,609 A | 11/1990 | Pawlos | |
| 4,999,034 A * | 3/1991 | Mager et al. | 96/117.5 |
| 5,060,480 A * | 10/1991 | Saulnier | 62/616 |
| 5,163,297 A | 11/1992 | Yani et al. | |
| 5,295,355 A | 3/1994 | Zhou et al. | |
| 5,388,413 A * | 2/1995 | Major et al. | 62/640 |
| 5,558,139 A * | 9/1996 | Snyder | 141/95 |
| 5,584,194 A | 12/1996 | Gardner | |
| 5,667,566 A * | 9/1997 | Flynn et al. | 96/117.5 |
| 5,697,228 A * | 12/1997 | Paige | 62/615 |

(Continued)

FOREIGN PATENT DOCUMENTS

EP 0221887 10/1987

(Continued)

*Primary Examiner* — Mohammad M Ali
(74) *Attorney, Agent, or Firm* — Michael W. Haas

(57) ABSTRACT

The present invention provides a removably attachable compact desiccant cartridge that is useful in lowering the dew point of a medically useful gas, which is liquefied by a cryogenic device. The desiccant cartridge of the present invention comprises a gas feedstream inlet, a dehumidifying zone which comprises a desiccant material, and a dehumidified gas feedstream outlet. The present invention also provides a method for using the same.

21 Claims, 9 Drawing Sheets

U.S. PATENT DOCUMENTS

| | | | |
|---|---|---|---|
| 5,700,310 A * | 12/1997 | Bowman et al. | 95/45 |
| 5,709,203 A | 1/1998 | Gier | |
| 5,893,275 A | 4/1999 | Henry | |
| 5,908,053 A | 6/1999 | Byrd | |
| 5,979,440 A | 11/1999 | Honkonen et al. | |
| 5,988,165 A | 11/1999 | Richey, II et al. | |
| 6,212,904 B1 * | 4/2001 | Arkharov et al. | 62/615 |
| 6,314,957 B1 | 11/2001 | Boissin et al. | |
| 6,327,862 B1 | 12/2001 | Hanes | |
| 6,358,300 B1 * | 3/2002 | Fornof et al. | 95/91 |
| 6,520,176 B1 * | 2/2003 | Dubois et al. | 128/200.24 |
| 6,641,644 B2 * | 11/2003 | Jagger et al. | 95/96 |
| 6,651,653 B1 | 11/2003 | Honkonen et al. | |
| 6,681,764 B1 | 1/2004 | Honkonen et al. | |
| 6,698,423 B1 * | 3/2004 | Honkonen et al. | 128/201.21 |
| 6,789,288 B2 * | 9/2004 | Wijmans et al. | 15/188 |
| 6,858,068 B2 * | 2/2005 | Smith et al. | 96/127 |
| 6,866,950 B2 * | 3/2005 | Connor et al. | 429/13 |
| 2004/0045315 A1 | 3/2004 | Kamoshita et al. | |
| 2004/0221475 A1 * | 11/2004 | Theriault | 34/523 |

FOREIGN PATENT DOCUMENTS

| | | |
|---|---|---|
| GB | 1416163 | 12/1975 |
| JP | 9-249811 A * | 9/1997 |
| JP | 2004085167 | 3/2004 |
| WO | WO 98/58219 | 12/1998 |

* cited by examiner

MOISTURE CONTENT OF SATURATED AIR

| degree F | grains/cubic ft. | degree F | grains/cubic ft. | degree F | grains/cubic ft. | degree F | grains/cubic ft. | degree F | grains/cubic ft. |
|---|---|---|---|---|---|---|---|---|---|
| 130 | 44.53 | 90 | 14.958 | 50 | 4.107 | 10 | 0.773 | -30 | 0.0941 |
| 129 | 43.40 | 89 | 14.528 | 49 | 3.963 | 9 | 0.736 | -31 | 0.0888 |
| 128 | 42.32 | 88 | 14.098 | 48 | 3.826 | 8 | 0.702 | -32 | 0.0838 |
| 127 | 41.27 | 87 | 13.687 | 47 | 3.691 | 7 | 0.668 | -33 | 0.0790 |
| 126 | 40.22 | 86 | 13.276 | 46 | 3.562 | 6 | 0.637 | -34 | 0.0746 |
| 125 | 39.22 | 85 | 12.887 | 45 | 3.453 | 5 | 0.606 | -35 | 0.0703 |
| 124 | 38.22 | 84 | 12.498 | 44 | 3.315 | 4 | 0.576 | -36 | 0.0662 |
| 123 | 37.25 | 83 | 12.129 | 43 | 3.195 | 3 | 0.549 | -37 | 0.0624 |
| 122 | 36.30 | 82 | 11.760 | 42 | 3.082 | 2 | 0.522 | -38 | 0.0588 |
| 121 | 35.36 | 81 | 11.410 | 41 | 2.970 | 1 | 0.496 | -39 | 0.0554 |
| 120 | 34.45 | 80 | 11.060 | 40 | 2.862 | 0 | 0.473 | -40 | 0.0521 |
| 119 | 33.56 | 79 | 10.720 | 39 | 2.759 | -1 | 0.4492 | -41 | 0.0490 |
| 118 | 32.70 | 78 | 10.396 | 38 | 2.657 | -2 | 0.4272 | -42 | 0.0462 |
| 117 | 31.84 | 77 | 10.073 | 37 | 2.561 | -3 | 0.4061 | -43 | 0.0430 |
| 116 | 31.01 | 76 | 9.758 | 36 | 2.466 | -4 | 0.3861 | -44 | 0.0409 |
| 115 | 30.19 | 75 | 9.461 | 35 | 2.375 | -5 | 0.3666 | -45 | 0.0384 |
| 114 | 29.41 | 74 | 9.164 | 34 | 2.286 | -6 | 0.3483 | -46 | 0.0361 |
| 113 | 28.62 | 73 | 8.880 | 33 | 2.202 | -7 | 0.3306 | -47 | 0.0339 |
| 112 | 27.85 | 72 | 8.596 | 32 | 2.118 | -8 | 0.3141 | -48 | 0.0318 |
| 111 | 27.12 | 71 | 8.330 | 31 | 2.027 | -9 | 0.2980 | -49 | 0.0299 |
| 110 | 26.39 | 70 | 8.063 | 30 | 1.940 | -10 | 0.2829 | -50 | 0.0280 |
| 109 | 25.687 | 69 | 7.809 | 29 | 1.856 | -11 | 0.2683 | -51 | 0.0263 |
| 108 | 24.988 | 68 | 7.560 | 28 | 1.776 | -12 | 0.2546 | -52 | 0.0247 |
| 107 | 24.319 | 67 | 7.315 | 27 | 1.698 | -13 | 0.2413 | -53 | 0.0232 |
| 106 | 23.560 | 66 | 7.079 | 26 | 1.624 | -14 | 0.2287 | -54 | 0.0217 |
| 105 | 23.010 | 65 | 6.852 | 25 | 1.553 | -15 | 0.2168 | -55 | 0.0203 |
| 104 | 22.370 | 64 | 6.630 | 24 | 1.485 | -16 | 0.2054 | -56 | 0.0190 |
| 103 | 21.761 | 63 | 6.411 | 23 | 1.419 | -17 | 0.1946 | -57 | 0.0178 |
| 102 | 21.151 | 62 | 6.205 | 22 | 1.354 | -18 | 0.1842 | -58 | 0.0167 |
| 101 | 20.568 | 61 | 6.000 | 21 | 1.295 | -19 | 0.1745 | -59 | 0.0156 |
| 100 | 19.968 | 60 | 5.803 | 20 | 1.236 | -20 | 0.1648 | -60 | 0.0146 |
| 99 | 19.436 | 59 | 5.607 | 19 | 1.181 | -21 | 0.1563 | -65 | 0.01043 |
| 98 | 18.883 | 58 | 5.419 | 18 | 1.127 | -22 | 0.1479 | -70 | 0.00738 |
| 97 | 18.359 | 57 | 5.236 | 17 | 1.076 | -23 | 0.1399 | -75 | 0.00517 |
| 96 | 17.834 | 56 | 5.061 | 16 | 1.027 | -24 | 0.1323 | -80 | 0.00359 |
| 95 | 17.327 | 55 | 4.894 | 15 | 0.980 | -25 | 0.1251 | -85 | 0.00246 |
| 94 | 16.820 | 54 | 4.720 | 14 | 0.935 | -26 | 0.1182 | -90 | 0.00167 |
| 93 | 16.344 | 53 | 4.562 | 13 | 0.891 | -27 | 0.1117 | -95 | 0.00113 |
| 92 | 15.868 | 52 | 4.410 | 12 | 0.850 | -28 | 0.1055 | -100 | 0.00075 |
| 91 | 15.413 | 51 | 4.256 | 11 | 0.810 | -29 | 0.0997 | -105 | 0.00045 |

Saturated Air = 100% Relative Humidity
Dewpoint = Saturated Air at a Given Temperatrure

Fig. 16

DESICCANT CARTRIDGE

FIELD OF THE INVENTION

This invention relates to a desiccant cartridge and a method for using the same in liquefaction of a medically useful gas.

BACKGROUND OF THE INVENTION

A number of people, typically elderly, suffer from chronic respiratory insufficiency due to restrictive airway disease, obstructive pulmonary disease, neuromuscular disorders or other complications. Symptoms of chronic respiratory insufficiency include shortness of breath, weight loss, headaches and sleeplessness.

To alleviate these symptoms, physicians often prescribe to these patients use of concentrated oxygen, i.e., an oxygen enriched gas. While some patients have their concentrated oxygen delivered to them as liquid oxygen or in high pressure oxygen cylinders, a great number of the patients use a small portable commercially available oxygen concentrator to obtain their supply of concentrated oxygen. Exemplary portable oxygen concentrator include Respironics Millenium Model 605 Oxygen Concentrator (Resperonics, Kennesaw, Ga.), AirSep NewLife Oxygen Concentrator (AirSep Corp., Buffalo, N.Y.), Puritan-Bennett Aeris 590 model Oxygen Concentrator, (Puritan-Bennett Corp., Pleasanton, Calif.), as well as those disclosed in U.S. Pat. No. 5,893,275, which is incorporated herein by reference in its entirety. Some patients use these portable oxygen concentrators in combination with an oxygen liquefaction device to produce liquid oxygen.

Liquid oxygen can be stored and transferred to other portable vessels, thereby allowing the patients a freedom of movement without having to be near the oxygen concentrator. One of the major problems with a conventional portable gas liquefaction device is the accumulation frost (i.e., rime) within the cryogenic unit of the device. Frost formation on the cryogenic unit forms an insulating barrier, which reduces the efficiency of the cryogenic unit, and hence the liquefaction rate of the oxygen enriched gas. In addition, a severe frost accumulation can cause partial or full blockage of the gaseous or liquefied oxygen flow through the device, thus potentially creating a dangerous situation. To prevent blockage, the cryogenic unit must be powered down and defrosted at regular intervals. Typically, the cryogenic unit is defrosted at least once a month. However, the actual frequency of defrosting the cryogenic unit depends on a variety of factors, such as the amount of moisture in the oxygen enriched gas, the amount of moisture in the transfill gas, the humidity and temperature at which the cryogenic device is used, as well as other factors that effect the frost formation. Powering down the cryogenic unit obviously has disadvantages, such as inability to use the unit as well as generally requiring periodic, expensive deliveries of supplemental liquid oxygen during the time it is being defrosted.

Therefore, there is a need for a device that reduces the frequency of cryogenic unit power downs.

BRIEF DESCRIPTION OF THE DRAWINGS

FIG. 16 is a table from Pneumatic Professionals, Incorporated showing the amount of moisture in moisture saturated air at various temperatures.

SUMMARY OF THE INVENTION

Figure 1:
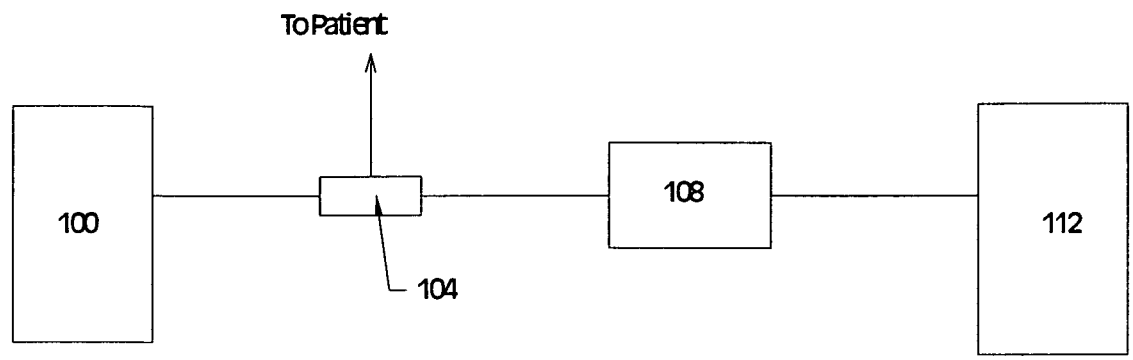
FIG. 1 is a schematic representation of a portable gas liquefying apparatus comprising a portable gas feedstream generating device, a desiccant cartridge, and a portable cryo-cooling device and an optional gas feedstream splitter (e.g., T-joint) for diverting at least a portion of the gas feedstream to the patient.

One aspect of the present invention provides a removably attachable desiccant cartridge for dehumidifying a gas feedstream in a portable gas liquefying apparatus and a method for using the same. The desiccant cartridge of the present invention is particularly useful in a portable gas liquefying apparatus that is used to liquefy medically useful gases, such as nitrogen, oxygen, argon, air, and a mixture thereof. Preferably, the desiccant cartridge of the present invention is compact and portable. By dehumidifying at least a portion of a medically useful gas feedstream using the desiccant cartridge of the present invention prior to its liquefaction, the amount of rime formation is reduced significantly resulting in less frequent down time of the cryogenic unit. In addition, reduction in the moisture content reduces the net effective dew point of the gas feedstream and increases the overall efficiency of the cryogenic unit.

The desiccant cartridge of the present invention can be used with any gas feedstream generating device, such as a pressurized gas cylinder, a compressor, and a portable gas concentrator, including an oxygen concentrator, such as Respironics Millenium Model 605 Oxygen Concentrator (Resperonics, Kennesaw, GA), AirSep NewLife Oxygen Concentrator (AirSep Corp. Buffalo, N.Y.), Puritan-Bennett Aeris 590 model Oxygen Concentrator, (Puritan-Bennett Corp., Pleasanton, Calif.), and those disclosed in U.S. Pat. No. 5,893,275, as well as other oxygen concentrators that are commercially available.

In one embodiment of the present invention, the desiccant cartridge comprises a gas feedstream inlet, a dehumidifying zone in communication with the gas feedstream inlet, and a dehumidified gas feedstream outlet in communication with the dehumidifying zone. The gas feedstream inlet is adapted to receive a gas feedstream from a gas feedstream generating device. And the dehumidified gas feedstream outlet is adapted to allow transfer of the dehumidified gas feedstream to a cryogenic unit. Preferably, the gas feedstream inlet and the dehumidified gas feedstream outlet of the desiccant cartridge form a hermetic seal with a respective devices to which they are attached to, thereby minimizing or preventing any leakage.

The dehumidifying zone preferably comprises a traversing gas flow path and is filled with a desiccant material that is capable of dehumidifying at least a portion of the gas feedstream flowing through the dehumidifying zone. The traversing gas flow path within the cartridge provides a longer dehumidifying zone length than the overall dimension of the desiccant cartridge, thus providing a longer contact time between the gas feedstream and the desiccant material, thereby resulting in more efficient dehumidification of the gas feedstream. The dehumidified gas outlet is in communication with a cryogenic unit, which is used to liquefy at least a portion of the dehumidified gas feedstream.

When the gas feedstream generating device is a medically useful gas concentrator, such as an oxygen concentrator, the desiccant cartridge of the present invention is preferably attached to the outlet of the medically useful gas concentrator. However, it should be appreciated that the desiccant cartridge of the present invention can be in fluid communication along any portion or section between the gas feedstream generating unit and the inlet portion of a cryogenic unit. For example, in an apparatus where the oxygen concentrator and the cryogenic devices are separate devices, the desiccant cartridge of the present invention can be removably attached directly to the oxygen concentrating unit (e.g., molecular sieve bed outlet of a non-cryogenic oxygen concentrator) or to the external outlet of the oxygen concentrator device. Alternatively, the outlet of the desiccant cartridge can be removably attached to the inlet portion of the cryogenic device and the inlet of the desiccant cartidge can be removably attached to a conduit (e.g., tubing) which is connected to a gas feedstream generating unit. In another embodiment, the desiccant cartridge can be removably attached within the internal section of the cryogenic device, e.g., immediately prior to the cryogenic unit itself. It should be appreciated that the above described configurations are only illustrative configurations of various components of the overall apparatus of the present invention, and the present invention is not limited to these particular configurations. All possible configurations of each components of the overall apparatus is within the scope of the present invention.

Other aspects of the present invention include (i) a method for using the desiccant cartridge; (ii) an apparatus which comprises a portable gas feedstream, a portable cryogenic device and the desiccant cartridge; (iii) a portable apparatus for producing a liquefied medically useful gas, wherein the portable appratus comprises a desiccant cartridge; (iv) a non-cryogenic gas separating apparatus comprising a desiccant cartridge; (v) a method for reducing the amount of frost formation on or near a cryogenic unit during production of a medically useful liquefied gas; (vi) a method for increasing the efficiency of a portable cryogenic device by reducing the moisture content of a gas feedstream; and (vii) a method for producing and storing a medically useful gas.

DETAILED DESCRIPTION OF THE INVENTION

Definitions

The terms "cryogenic" and "cryocooling" are used interchangeably herein and relate to a process of producing or achieving a very low temperature, which allows liquefaction of a medically useful gas.

Unless the context requires otherwise, the term "device" is used to denote the overall system, where as the term "unit" is used to denote a specific portion of the system that is responsible for a particular function. For example, a "cryogenic device" refers to an overall system that is used in liquefaction of a medically useful gas, including the "cryogenic unit" (which refers to a portion or a section of the cryogenic device where the actual liquefaction of a gas occurs, e.g., cold finger and a liquid collection vessel), the power supply, casing, tubing, etc. Similarly, a "gas (e.g., oxygen) concentrator device" refers to an overall system that is used in producing an oxygen enriched gas, including a "gas concentrator unit" (which refers to a portion or a section of the gas concentrator device where the actual concentration of a gas occurs, e.g., molecular sieve bed in a non-cryogenic gas concentrator device.

The terms "dehumidifying" and "drying" are used interchangeably herein and refer to removing at least a portion of water molecule that is present in a gas feedstream.

"Desiccant" refers to a material that is capable of reducing the amount of moisture present in a gas or a gas feedstream.

"Dew point" refers to an effective temperature at which the moisture that is present in a gas feedstream condenses.

"Enriched" means the concentration of a gas is higher than its naturally occurring (i.e., ambient) concentration.

"Gas" refers to a compound or composition that is in a gaseous state at ambient temperature and pressure.

"Medically useful gas" refers to one or more components of air. Exemplary medically useful gases include oxygen, nitrogen, argon, air and mixtures thereof. Preferred medically useful gases are oxygen and/or nitrogen enriched gases.

When describing a gas flow path, the term "traversing" refers to a gas flow path that changes direction. Each directional change may be independently a sharp or a gradual change. In addition, each directional change can comprise up-and-down and/or side-to-side directional changes. Exemplary traversing gas flow paths include, but are not limited to, zigzag flow paths, circuitous paths, sinusoidal-shaped flow paths, coil-like or helical flow paths, any combination thereof, and other traversing flow path configurations.

When referring to a reduction in the dew point of a dehumidified gas, the dew point reduction refers to the reduction of the dew point relative to the same gas without a prior treatment with the desiccant cartridge of the present invention.

"Transfill gas" refers to a gas that is used to transfer a liquefied gas from a portable liquefaction device to a vessel or a container.

Overview

A variety of portable gas liquefying devices are available today for liquefying medically useful gases. These gas liquefying devices are used in a wide variety of settings and applications including as an at home oxygen liquefaction apparatus for patients with respiratory insufficiency. While a variety of gases are medically useful and known to one skilled in the art, for the sake of brevity and clarity, the present invention will now be described in reference to liquefying an oxygen enriched gas or gas feedstream. However, it should be appreciated that the present invention is also applicable to liquefying other gases, in particular to other medically useful gases, such as nitrogen, argon, air, and any mixtures thereof.

Portable oxygen liquefaction devices are useful for producing small volumes of liquid oxygen in remote locations, especially the homes of patients with respiratory insufficiency. These devices are generally free-standing devices having a small enough size that can be accommodated in most home environments. Exemplary portable liquid oxygen liquefaction devices include those disclosed in U.S. Pat. No. 5,893,275 and references cited therein, all of which are incorporated herein by reference in their entirety.

Portable oxygen liquefaction devices can also comprise a gas separation unit for separating oxygen from an input fluid, such as air, to form an oxygen enriched gas feedstream, and a cryogenic unit for liquefying at least a portion of the oxygen enriched gas feedstream. The oxygen separation unit and the cryogenic unit can be part of a single device or they can be two distinct devices or components that are in fluid communication with each other.

The medically useful gas feedstream can be derived from other sources, for example, via pressurized gas cylinder or a compressor (e.g., for liquefying air). Accordingly, the source of a gas feedstream is not limited to those explicitly disclosed herein. In fact, it is contemplated that any and all gas feedstreams known to one skilled in the art are encompassed within the scope of the present invention.

One of the major problems with conventional portable oxygen liquefaction devices is the accumulation frost (i.e., rime) within the cryogenic unit of the device. Frost formation on the cryogenic unit (e.g., the cold finger portion) forms an insulating barrier, which reduces the efficiency of the cryogenic unit. Frost formation on the cryogenic unit also results in a reduction of the liquefaction rate of oxygen. In addition, a severe frost accumulation can cause partial or full blockage of the gaseous or liquid oxygen flow through the device, thereby creating a potentially dangerous situation.

Moisture that is present in ambient air and/or the gas feedstream is believed to be the major cause of frost formation. Moreover, the dew point of an oxygen enriched feedstream can vary depending on the amount of moisture that is present in the oxygen enriched gas feedstream. In general, however, the dew point in an oxygen enriched gas feedstream that is generated by a conventional portable oxygen concentrator ranges from about −30° C. to −47° C. depending on a variety of factors, such as, but not limited to, the temperature and humidity of ambient air, the type of oxygen concentrator device used, the flow rate of oxygen enriched gas feedstream, the length of conduit (e.g., tubing) between the oxygen enriched gas feedstream source (e.g., oxygen concentrator) and the cryogenic unit (or device), and the moisture permeability of conduits (e.g., tubing).

The amount of moisture present in the transfill air also has a significant influence on the rate and the amount of frost formation within the cryogenic device. For example, if one transfill is used per day requiring about 8 liters of air per transfill, this would typically add an additional 0.9 grams/month to 5.0 grams/month of moisture to the cryogenic unit.

The formation of frost on the cryogenic unit or the cold finger portion reduces the efficiency of the cryogenic unit and is inconvenient in that it requires the entire unit to be powered down and cleaned. Devices and methods of the present invention increase the efficiency of the cryogenic unit by reducing the moisture content of the gas feedstream and/or the transfill air that comes in contact with the cryogenic unit. In particular, the present invention provides a removably attachable desiccant cartridge for dehumidifying a gas feedstream and/or the transfill air.

Gas Feedstream

A wide variety of sources and methods are available for providing a gas feedstream to a cryogenic unit. For example, the gas feedstream can be provided by an external source, such as a compressor or a pressurized gas cylinder, or it can be generated by a gas separation unit, such as The Respironics Millenium Model 605 Oxygen Concentrator (Respironics, Kennesaw, Ga.) and the AirSep NewLife Oxygen Concentrator (AirSep Corp., Buffalo, N.Y.). The gas separation unit can be based on any number of oxygen concentrating techniques known to one skilled in the art, including, a cryogenic unit, non-cryogenic unit, and a combination thereof. A cryogenic gas separation unit utilizes the boiling point difference between oxygen and other gases to enrich or separate oxygen. A non-cryogenic gas separation unit typically uses a physical means to enrich oxygen gas. Preferably, the gas feedstream is generated by a non-cryogenic gas separation unit, and more preferably one that is capable of enriching one or more components of air. There are a variety of non-cryogenic gas separation methods that are available, including, but not limited to, devices that are based on the adsorptive processes (e.g., molecular sieves), membranes, ceramics, ionic conductors, and other devices and processes known to one skilled in the art.

In adsorptive processes, the gas separator can include one or more vessel(s) containing a gas adsorptive medium that can separate different gas(es) based on a variety of properties, such as size, polarity (i.e., dipole moment), density, and other physical properties. Exemplary gas adsorptive mediums that separate different gases based on the molecular size include, molecular sieves such as zeolites. Preferably, such molecular sieves have pore size and other characteristics as to preferably absorb one particular gas, e.g., nitrogen, over the other gas, e.g., oxygen. In this manner, when the air is passed through a bed of molecular sieves, nitrogen and other gases, such as carbon dioxide, are adsorbed onto the molecular sieves. These adsorbed gases can then released from the bed, preferably at a lower pressure, when the molecular sieve becomes saturated or inefficient. This cycle of adsorption and release can be repeated. In addition, a multiplicity of oppositely cycled adsorbent beds can be used to assure a continuous flow of concentrated oxygen enriched gas feedstream or a double or single bed with a properly sized accumulator vessel.

In membrane separation, the separator comprises one or more, preferably a plurality of, membranes. Each of the membranes has a high pressure gas (such as the compressed gas for the first membrane) on an upstream side and low pressure (filtered) gas on a downstream side. In this manner, the oxygen and water vapor in the high pressure gas contacting the upstream side of a membrane pass through the membrane to the low pressure side of the membrane to form oxygen enriched filtered gas feedstream. In conventional portable gas liquefaction devices that use membrane separation for concentrating oxygen, the high pressure gas has a pressure typically ranging from about 7 to about 14 atm and the low pressure gas has a pressure typically ranging from about atmospheric to about 1.5 atm. It is also possible in membrane separation to reverse the order of the compressor and of the separator such that the compressor acts as a vacuum pump and provides suction on the low pressure, downstream side where the oxygen enriched gas will be produced. A plurality of membranes connected in series may be required to realize a high level of purity of the molecular oxygen in the concentrated gas.

In ionic conduction, the gas separator typically includes a conductive membrane and it may also include a voltage source for biasing the membrane. Alternatively, the driving force can be provided by a pressure difference between the upstream side and the downstream side of the high temperature membrane.

Cryogenic Unit

The cryogenic (i.e., cryocooler) device on conventional portable gas liquefaction devices typically include a cryocooler unit and a condensation unit that is in thermal communication with the cryocooler unit. Exemplary cryogenic devices include Home-Away System™ by In-X Corp. (Denver, Colo.), cryogenic devices disclosed in U.S. Pat. No. 6,212,904 as well as those disclosed in the references cited therein, all of which are incorporated herein by reference in their entirety. The liquid product resulting from the cryogenic unit is typically stored in a reservoir or vessel. Some portable oxygen liquefaction devices also include an additional refrigeration device, such as a conventional refrigerator, for cooling a heat rejection unit of the cryocooler unit.

Apparatuses of the present invention can also include one or more bypass valves. These bypass valves can be located between the gas separating device and the cryocooler device. In this manner, these bypass valves can be used to remove a portion of the oxygen enriched feedstream, which can be used to provide a portion of the oxygen enriched feedstream directly to the patient, or for sampling the oxygen enriched gas feedstream for monitoring purposes. In addition, these bypass valves allow the patient, who is located in the vicinity of the device, to inhale the diverted oxygen enriched feedstream directly without interrupting the balance of the feedstream flowing to the cryogenic unit of the apparatus.

Desiccant Cartridge

Desiccant cartridges of the present invention are compact, disposable, and/or portable, and are useful in any variety of portable gas liquefaction devices. In particular, the desiccant cartridge of the present invention is useful in a portable gas liquefying apparatuses that are used to liquefy medically useful gases. For example, desiccant cartridges of the present invention can be used in conjunction with the gas liquefaction devices disclosed in the above incorporated U.S. Pat. Nos. 6,212,904 and 5,893,275.

As stated above, the desiccant cartridges of the present invention are compact and portable. In one particular embodiment, the desiccant cartridge has a dimension of about 8.25 inches (width) 7.25 inches (height) and 1.5 inches (depth). However, it should be appreciated that other desiccant cartridge dimensions are also within the scope of the present invention. The shape of desiccant cartridges of the present invention is not crucial to its utility. Accordingly, all shape of desiccant cartridges are within the scope of the present invention as long as the overall design allows a compact configuration in which the length of the dehumidifying zone, infra, is preferably significantly longer than the length of the overall design. Exemplary desiccant cartridge configurations include, block-shape, oval, helical or coil-like, conical, cylindrical or tubular, rectangular, pyrimidal, hemi-spherical, etc. Typically, the total volume of the dehumidifying zone ranges from about 20 cubic inches to about 100 cubic inches, preferably from about 25 to 80 cubic inches and most preferably about 60 cubic inches. However, it should be appreciated that the scope of the present invention is not limited to these desiccant cartridge volumes. The actual dehumidifying zone volume will depend on a variety of factors, such as the desiccant material used, the length of the desiccant cartridge's life cycle desired, etc.

The desiccant cartridge of the present invention will now be illustrated in reference to the accompanying drawings. In the drawings, the same element in a different configuration or view is indicated by the identical numbering. In FIG. 1, a portable oxygen concentrator 100 is used to generate an oxygen enriched feedstream. However, as stated above, the source of oxygen enriched feedstream can be an oxygen gas tank or other suitable devices and means known to one skilled in the art. This oxygen enriched feedstream is fed through an optional bypass valve 104. The optional bypass valve 104 allows the oxygen enriched gas to be delivered directly to the patient, if desired. The oxygen enriched feedstream is then introduced into the desiccant cartridge 108, which removes at least a portion of the moisture that is present in the oxygen enriched feedstream to produce a dehumidified oxygen enriched feedstream. The dehumidified oxygen enriched feedstream is then fed to a cryogenic device 112, which liquefies at least a portion of the dehumidified oxygen enriched feedstream.

Figure 2:
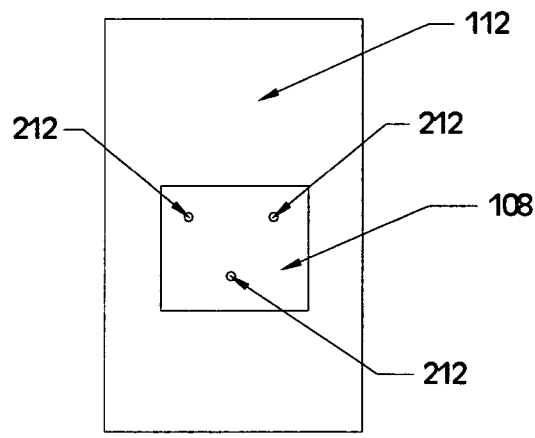
FIG. 2 is a schematic illustration of one embodiment of a desiccant cartridge of the present invention that is removably attached to a cryogenic unit.

FIG. 1 depicts an apparatus in which desiccant cartridge 108 is a separate unit from cryogenic device 112, whereas FIG. 2 illustrates a configuration in which desiccant cartridge 108 is removably attached to cryogenic device 112. In the configuration illustrated in FIG. 2, the enriched oxygen feedstream is connected to cryogenic device 112. The enriched oxygen feedstream flows through desiccant cartridge 108 prior to being liquefied by cryogenic device 112. The enriched oxygen feedstream can be attached directed to desiccant cartridge 108 or it can be attached to cryogenic device 112 which is then diverted through desiccant cartridge 108 prior to its liquefaction.

Desiccant cartridge 108 can be removably attached within the interior of portable oxygen concentrator device 100 or cryogenic device 112 (not shown). Alternatively, desiccant cartridge 108 can be removable attached on the outside of portable oxygen concentrator device 100 or cryogenic device 112. Still further, desiccant cartridge 108 can be a separate device. All overall apparatus configurations that allow an oxygen enriched gas feedstream to be dehumidified prior to liquefaction is contemplated to be within the scope of the present invention.

Figure 3:
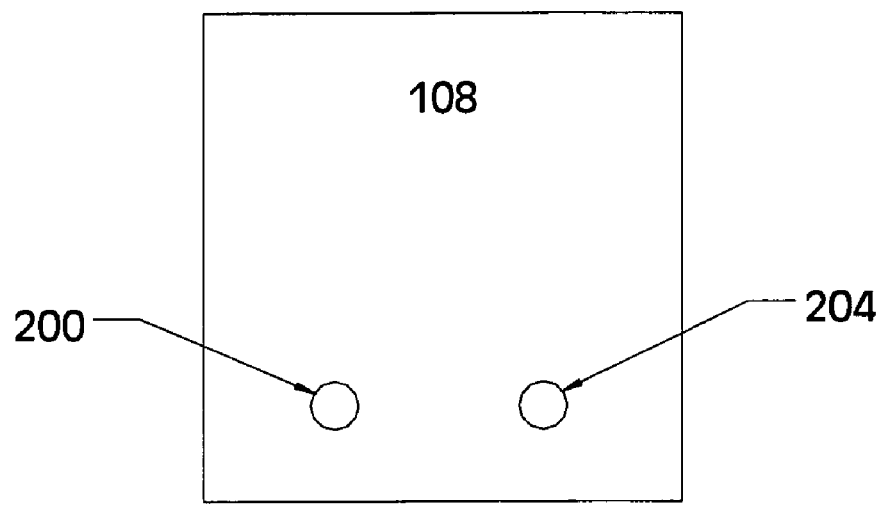
FIG. 3 is a schematic illustration of one embodiment of the desiccant cartridge of the present invention along with its corresponding inlet and outlet openings.
Figure 4:
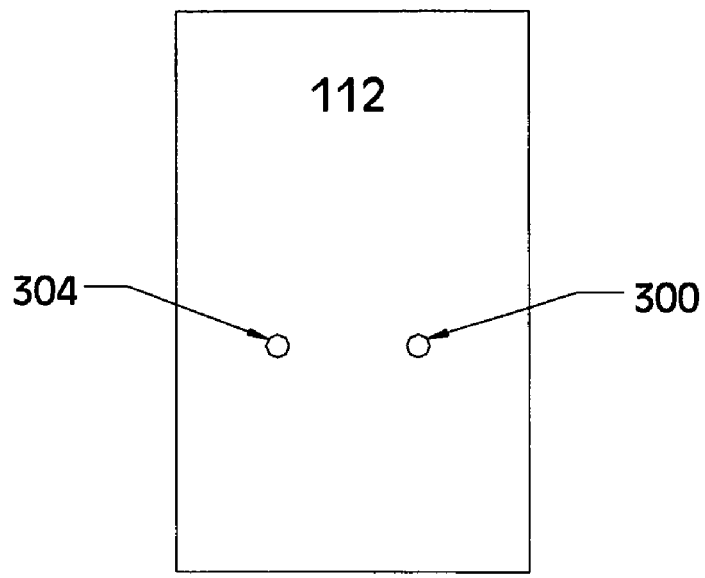
FIG. 4 is a schematic representation of a cryogenic unit with a gas feedstream inlet and outlet.

As shown in FIG. 3, desiccant cartridge 108 comprises an inlet 200 for introducing an oxygen enriched gas feedstream into desiccant cartridge 108. Desiccant cartridge 108 also comprises an outlet 204 where the dehumidified oxygen enriched gas feedstream exits desiccant cartridge 108. Preferably, inlet 200 and outlet 204 of desiccant cartridge 108 are hermetically sealed with a corresponding outlet of an oxygen enriched gas feedstream generating device (not shown) and inlet 304 of cryogenic unit 112 (see FIG. 4), respectively, to avoid or minimize leakage. In one particular embodiment, inlet 200 and outlet 204 of desiccant cartridge 108 comprise O-rings (not shown) that form a hermetic seal with the corresponding coupling components of oxgyen enriched gas feedstream concentrator device and cryogenic unit 108. Alternatively, Teflon® lip seals (not shown) can be used instead of O-rings. In this particular configuration, when desiccant cartridge 108 (not shown in FIG. 4) is attached to cryogenic device 112, an oxygen enriched gas feedstream enters cryogenic device 112 through a gas feedstream inlet (not shown) and exits through outlet 300 and enters desiccant cartridge 108. The dried (or dehumidified) oxygen enriched gas feedstream then exits outlet 204 and reenters cryogenic device 112 through inlet 304. Alternatively, cryogenic unit 112 and portable oxygen concentrator 100 (i.e., gas feedstream generating device, not shown in FIG. 4) can be a combined into a single unit (not shown). In this manner, the oxygen enriched gas feedstream is generated by an oxygen concentrator unit and exits the oxygen concentrator unit through outlet 300, which is attached to inlet 200 of desiccant cartridge 108. The oxygen enriched gas feedstream is then dehumidified by desiccant cartridge 108 and exits desiccant cartridge 108 through outlet 204 and reenters the apparatus via inlet 304, which is in fluid communication with cryogenic unit 112. This latter configuration allows for a one-piece design of the entire apparatus, thereby reducing the amount of space needed to operate the system. In addition, this one-piece design significantly reduces the amount of conduit (e.g., tubing) required to connect each components or units.

In addition to attaching desiccant cartridge 108 to cryogenic unit 112 via inlet 200 and outlet 204 coupling, other means of securing desiccant cartridge 108 to cryogenic unit 112 can also be provided. Exemplary securing means include, screws, hooks and loops (e.g., Velcro®), snap on mechanisms, latches, other securing means known to one skilled in the art, and a combination of two or more thereof. FIG. 2 illustrates desiccant cartridge 108 that is removably attached to cryogenic unit 112 via one or more screws 212. This additional securing means allows desiccant cartridge 108 to be firmly, yet removably, attached to cryogenic unit 112, thereby preventing an accidental detachment.

Figure 5:
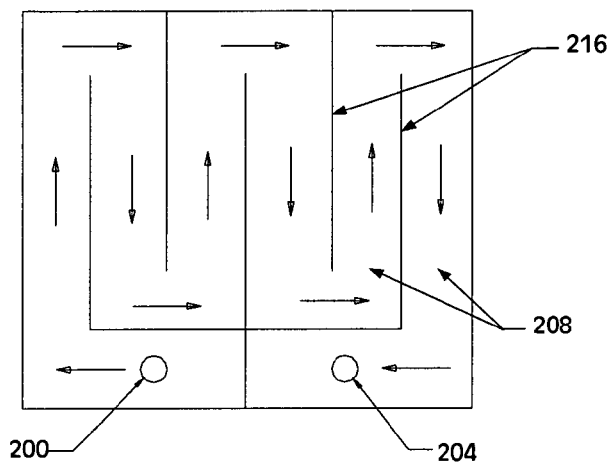
FIG. 5 is a cut away view of one particular design of the desiccant cartridge of the present invention showing the interior dividers which increase the net flow path within the desiccant cartridge.

As shown in FIG. 5, within the interior of desiccant cartridge 108 is a dehumidifying zone 208 that is divided by one or more dividers 216. Dividers 216 divides dehumidifying zone 208 into different sections, thereby forcing the oxygen enriched gas feedstream to traverse through different dehumidifying zones. This effectively increases the length of dehumidifying zone 208, thereby providing a longer contact time between the oxygen enriched gas feedstream and a desiccant material (not shown) that is present within dehumidifying zone 208. As indicated by the arrows in FIG. 5, the oxygen enriched gas feedstream enters desiccant cartridge 108 through inlet 200, passes through the desiccant material (not shown) that is present along the length of dehumidifying zone 208, and exits through outlet 204 where it is liquefied by cryogenic unit 112. As stated above, dehumidifying zone 208 is divided into different sections by dividers 216 to increase the contact time between the desiccant material and the oxygen enriched gas feedstream. It should be appreciated that dehumidifying zone 208 shown in FIG. 5 is only illustrative of the basic concept of the present invention. In practice, any suitable dehumidifying zone 208 configuration can be used. For example, the desiccant cartridge can be helical or a coil-like where one end of the coil is the inlet and the other end of the coil is the outlet of the desiccant cartridge. Alternatively, the helical or coil-like dehumidifying zone can be enclosed within a block-shaped desiccant cartridge configuration.

A wide variety of materials can be used to fabricate the desiccant cartridge of the present invention. Exemplary materials that are suitable for desiccant cartridge fabrication include, but are not limited to, plastics (including thermoplastics), fiber glass, glass, metal, and other materials that are generally considered to be substantially non-gas permeable. For ease of production and cost, however, desiccant cartridges of the present invention are typically made from plastics. Such plastics desiccant cartridges can be made by casting or using a mold.

By reducing the amount of moisture present in the oxygen enriched gas feedstream prior to liquefaction, desiccant cartridges of the present invention reduce the effective dew point of an oxygen enriched gas feedstream. While the actual dew point reduction varies depending on a variety of factors, e.g., humidity level, flow rate, rate of moisture adsorption by the desiccant material, etc., typically desiccant cartridges of the present invention reduce the dew point of an oxygen enriched gas feedstream by at least 5° C. (preferably at least by 10° C., and more preferably at least by 15° C.) compared to the same oxygen enriched gas feedstream in the absence of the desiccant cartridge.

Desiccant Materials

Any hygroscopic material can be used as a desiccant material in the present invention as long as the contact time with the oxygen enriched gas feedstream is sufficiently long enough to remove the moisture content to a desired level. Hygroscopic materials react with water, form a puddle and dissolve (deliquesce), physically entrap water molecules, form a bond (covalent, hydrogen or ionic) with water molecule, and/or retain water molecules within the material by other physical and/or chemical means. Exemplary hygroscopic materials include, but are not limited to, hydroxides (such as alkaline, alkaline-earth or transition metal hydroxides, e.g., sodium hydroxide, potassium hydroxide, calcium hydroxide, magnesium hydroxide), molecular sieves (such as zeolites), sulfates (such as magnesium sulfate), metal chlorides (e.g., sodium chloride, potassium chloride, and calcium chloride), silicates, and other hygroscopic materials known to one skilled in the art. While there are a variety of hygroscopic materials available that can be used as a desiccant material of the present invention, not all the materials are well suited. For example, hydroxide are caustic or corrosive, and therefore pose hazard in home environmental use, and metal chlorides have a low rate of water absorption, and therefore are not very effective in a compact design.

A particularly preferred desiccant material is molecular sieve. Molecular sieves are commercially available often as ceramic-appearing pellets or balls. Molecular sieves have one of the lowest dusting factor of any commercially available desiccant and do not change size or shape upon reaching saturation. Molecular Sieves are synthetically produced Zeolites characterized by pores and crystalline cavities of highly uniform dimensions. Other adsorbents of commercial importance are typically described as having "pore size ranges." The pore sizes of these adsorbents can vary widely on the face of the same particle. Molecular Sieves are available in several different grades. These grades are unique from one another, in part, due to their chemical composition and pore size. An especially preferred molecular sieve is Zeolite 3 Å (or type 3A). Type 3A (three angstrom) molecular sieve is the potassium form of the Zeolite. Type 3A will generally adsorb those molecules that are less than three angstroms in size (e.g., water, helium, hydrogen, and carbon monoxide).

Molecular sieves, as well as other desiccant materials, are typically available in a variety of particle sizes. It should be appreciated that smaller particle sized desiccant materials provide larger surface areas at a given volume. Therefore, it is generally preferred to use a smaller particle sized desiccant material. However, this benefit should be balanced with a difficulty in keeping the desiccant material within the confines of the desiccant cartridge. For example, one can use powdered molecular sieves which have a much larger overall surface area then a pellet form of molecular sieves. Unfortunately, a powdered form of molecular sieve can be easily blown out of the desiccant cartridge, due to a relatively high gas flow rate through the cartridge, and contaminate the liquified gas. Thus, a special means is required to keep the powdered molecular sieves confined to the interior of the desiccant cartridge, which may complicate the desiccant cartridge design and increase the overall production cost. In addition, using a smaller particle sized molecular sieves also result in a larger pressure drop across the desiccant cartridge (i.e., pressure difference between the inlet and the outlet). Accordingly, when using molecular sieves as the desiccant material, it is preferred to use molecular sieves with a particle size of about 8×12 mesh (i.e., about 1/16 inch in diameter). However, it should be appreciated that other sizes are also contemplated to be within the scope of the present invention.

One of the adsorption characteristic of molecular sieve is its ability to continue adsorption process at temperatures which would cause other desiccants to desorb trapped water molecules. In a gas drying device, water will continue to be adsorbed even though the process temperature may be in excess of 300° F. It must be understood, however, that the adsorption capacity of most desiccants is generally negatively affected by temperatures in excess of 100° F. Molecular sieves, though, retain their ability to adsorb water molecules over a much wider spectrum of temperatures than other desiccant materials. In addition, molecular Sieves typically also have a much higher equilibrium capacity for water vapor, compared to other desiccant materials, under very low humidity conditions. Accordingly, molecular sieves are very effective in reducing the water vapor content of gases, in most cases, to the parts per million range.

In another embodiment of the present invention, the desiccant cartridge can comprise an indicator that indicates the amount of moisture present in the desiccant material. The indicator can be an electronic based moisture sensor, such as hydrometers that are known to one skilled in the art (e.g., Shaw Super-Dew Hydrometer with Gray Spot Moisture Sensor and Radio Shack Cat. No 63-867A Thermometer/Hygrometer), or a simple color indicator that changes color depending on the amount of moisture present in the desiccant material. There are a variety of materials that are commercially available that change color depending on the amount of moisture it adsorbs or has reacted with. For example, some molecular sieves are blue in color when dry but changes to a different color when it adsorbs moisture. In addition, some solid magnesium sulfates are blue when dry and turns pink after it adsorbs moisture. For economical and convenience reasons, preferably the moisture level indicator is a color indicator, e.g., changes color depending on the amount of moisture it had adsorbed.

As stated above, some molecular sieves are moisture-indicating. These moisture-indicating molecular sieves have a substantially the same water adsorption capacity characteristics as non-moisture-indicating molecular sieves. In the active condition, moisture-indicating molecular sieve is often bright blue in color. As the molecular sieve adsorbs moisture and the relative humidity approaches about 10%, moisture-indicating molecular sieve turns a lighter blue color. As the desiccant progresses towards saturation, the color turns to buff. At this point, the molecular sieve or the entire desiccant cartridge can be replaced. Alternatively, the desiccant material, along with colored molecular sieves or other color based moisture indicator that is used in the desiccant cartridge, can be regenerated by drying the desiccant material and the indicator. For example, the desiccant material can be heated to release the adsorbed moisture and/or placed under a high vacuum to remove the moisture from the desiccant material. Generally, however, it is more economical and convenient to simply replace the entire desiccant cartridge.

Additional objects, advantages, and novel features of this invention will become apparent to those skilled in the art upon examination of the following illustrative examples thereof, which are not intended to be limiting.

EXAMPLES

Example 1

This example illustrates a method for measuring the dew point of oxygen enriched gas using a desiccant cartridge of the present invention over an extended period of time to determine the drying capacity and the life expectancy of the desiccant cartridge.

To simulate a prolonged use, an accelerated conditions are used to test the desiccant cartridge. Briefly, the method involves placing a desiccant cartridge (1.50 inch dia.×42 inches in length with Zeolite 3A-12 desiccant) in a small room at a humidity level of around 80% (e.g., using a 4 gallon humidifier by Kenmore, (Hoffman Estate, Ill.) until the capacity of the desiccant cartridge to remove moisture drops below an acceptable level. The rate of this test is accelerated by a factor of 5 times so the results can be achieved in a reasonable time period. Prior to starting the test, the dry desiccant cartridge is weighed. The dew point of a gas flowing through the desiccant cartridge is measured using a dew point meter (Shaw Super-Dew Hydrometer with Gray Spot Moisture Sensor, by (Shaw, Bradford, England) or Radio Shack Cat. No 63-867A Thermometer/Hygrometer by Tandy Corp. (Fort Worth, Tex.). The flow rate through the cartridge is also measured using a flow meter (Sierra Instruments, Inc., Monterey, Calif., Model 822-13-OV1 PV1-V1 Flowmeter).

A typical flow of oxygen from the concentrator (AirSep NewLife model Oxygen Concentrator, AirSep Corp, Buffalo, N.Y., or Puritan-Bennett Aeris 590 model Oxygen Concentrator, Puritan-Bennett Corp. Pleasanton, Calif.) through the desiccant cartridge is 1.1 liters/minute. To accelerate the test, the flow rate of 5.5 liters/minute is used. Since the concentrators are rated for a maximum flow rate of 5 liters/minute, two concentrators are used in combination to produce this flow rate. Also using two concentrators makes the test more accurate since a high flow rate is likely to lower the dew point of concentrated oxygen generated by the concentrators.

To transfill a 1.2 liter stroller with liquid oxygen (i.e., LOX) requires an ambient flow of about 8 liters of air. Therefore, for each day of the test using the transfill compressor (Thomas Compressor model #010CA26, Sheboygan, Wis.) from the Home-Away System (by In-X Corp. of Denver, Colo. ) flow 40 liters of room air through the desiccant cartridge. The following data are recorded for this test: date, time, room temperature (° F.), % relative humidity of the room, and the dew point of dried oxygen (° C.) over the duration of the test. At the end of the test, the weight of the spent desiccant cartridge is also measured to determine the amount of moisture absorbed.

Preferably, the cartridge lasts about 3 months, more preferably at least about 6 months or longer, when the device is operated in high humidity conditions. For the purpose of this test, a desiccant cartridge is considered to be spent (loaded with moisture) when the dew point of the dried oxygen rises above −50° C. At −50° C dew point the device is receiving moisture at a rate of about 1.8 grams/month.

Following formulas are used for various calculations:

Feed Flow of Oxygen Per Month $$(1.1 \text{ L/min}) \times (1440 \text{ min/day}) \times (30.5 \text{ day/month}) \times \frac{1}{1000} \text{ m}^3/\text{L} = 48.312 \text{ m}^3/\text{month}$$

Moisture Per Month in Feed Flow @ −30° C. Dew Point $$(48.312 \text{ m}^3/\text{month}) \times (0.333 \text{ g/m}^3) = 16.1 \text{ g/month}$$

Moisture Per Month in Feed Flow @ −47° C. Dew Point (48.312 m³/month)×(0.054 g/m³)=2.6 g/month Moisture Per Month in Feed Flow @ −50° C. Dew Point (48.312 m³/month)×(0.038 g/m³)=1.8 g/month Moisture Per Month in Feed Flow @ −70° C. Dew Point (48.312 m³/month)×(0.0029 g/m³)=0.14 g/month Transfill Flow of Ambient Air Per Month (8 L/day)×(30.5 day/month)×(¹⁄₁₀₀₀ m³/L)=0.244 m³/month Moisture Per Month in Transfill Flow at 80° F. and at 80% Relative Humidity (RH)

80° F.=27° C. Therefore 0.80×25.8 g/m³=20.6 g/m³

(0.244 m³/month)×(20.6 g/m³)=5.0 g/month

Moisture Per Month in Transfill @ 70° F. & 20% RH

70° F.=21° C. Therefore, 0.20×18.3 g/m³=3.7 g/m³

(0.244 m³/month)×(3.7 g/m³)=0.90 g/month

Moisture Per Month in Transfill @ −70° C. Dew Point (0.244 m³/month)×(0.0029 g/m³)=0.0007 g/month Example 2

This example shows the dew point of an oxygen enriched gas feedstream as a function of its moisture content.

A gas at cryogenic temperatures has a very low moisture saturation point. As the oxygen enriched gas flows through the condenser assembly across the cold finger, any moisture in the oxygen enriched feedstream flowing to the cryocooler will condense out. This moisture condenses out as frost that sticks to the cold surfaces. Some of this frost will eventually migrate down into the Dewar® flask and will float in the liquid oxygen. The frost that sticks to the cold surfaces inside the condenser assembly and on the cold finger can build up and reduce the liquefaction rate of the device. The data gathered by this testing can be used to establish test conditions for additional testing to be performed on operating a portable oxygen liquefaction device (e.g., Home-Away Systems, manufactured by In-X Corp of Denver, Colo.) in conjunction with a desiccant cartridge of the present invention. Such a test will determine how often the portable oxygen liquefaction device need to be de-rimed by the user to remove the frost buildup.

Figure 6:
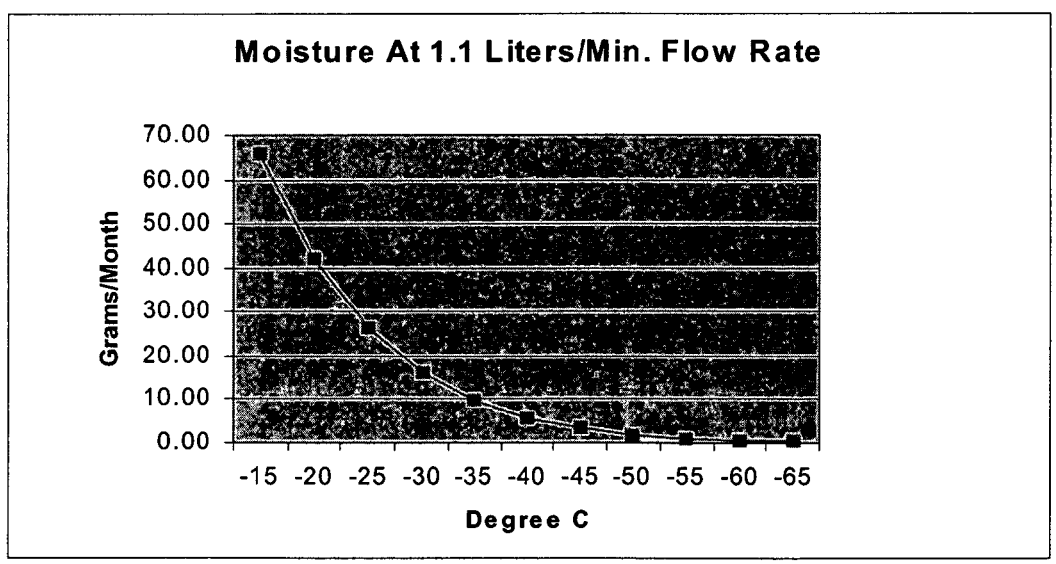
FIG. 6 is a graph showing a relationship between the dew point and the moisture content of an oxygen enriched gas feedstream

In order to gain a better understanding of variation in the moisture content in the oxygen flow going to the cryocooler, a hydrometer (i.e., dew point Meter) was used to measure the dew points. A series of tests was run measuring the dew point of the oxygen enriched gas feedstream under a variety conditions, e.g., temperature, humidity, etc. The dew point measurements was converted to the mass of moisture in one month (30 days) of oxygen feed flow assuming a flow rate of 1.1 L/min. (See Example 1 above for the formulas used in calculations). As shown in FIG. 6, there is an exponential relationship between the dew point and moisture content of the oxygen enriched gas feedstream.

Example 3

This example measures the impact of moisture entry via diffusion through tubing in a Puritan Bennett 1.2 liter stroller (Puritan-Bennett, Pleasanton, Calif.).

The dew points were measured on the oxygen boiling off from a Puritan Bennett 1.2 liter stroller under three different test conditions.

From Stroller Patient Output with no Tubing

| Ambient Temp. | Rel. Hum. | O₂ Dew Point | Moisture/Month |
|---|---|---|---|
| 76° F. | 22% | −62.4° C. | 0.39 g/month |

From Stroller Patient Output Through 12 Feet of Bev-A-Line Tubing 10 Feet of Tubing in Humidity Chamber.

| Ambient Temp. | Rel. Hum. | O₂ Dew Point | Moisture/Month |
|---|---|---|---|
| 95° F. | 62% | −49.7° C. | 1.87 g/month |

From Stroller Patient Output Through 12 Feet of Vinyl Tubing 10 Feet of Tubing in Humidity Chamber.

| Ambient Temp. | Rel. Hum. | O₂ Dew Point | Moisture/Month |
|---|---|---|---|
| 95° F. | 58% | −41.6° C. | 4.70 g/month |

Figure 7:
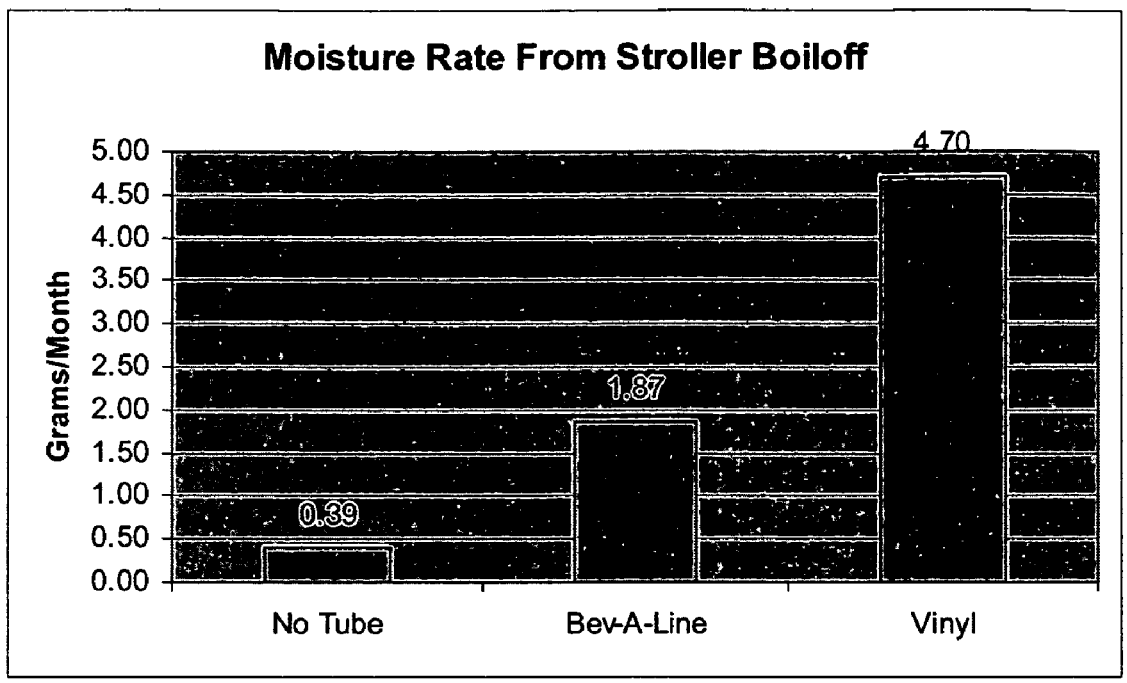
FIG. 7 is a bar graph showing a rate of moisture diffusion through different tubing materials.

The results of this test show that significant moisture can enter the gas feedstream by diffusion through the tubing. As expected, the use of a less permeable Bev-A-Line tubing resulted in a lower moisture then the vinyl. See FIG. 7.

Example 4

This example illustrates the moisture content of various oxygen enriched feedstreams that are generated using AirSep Oxygen Concentrator (Airsep Corp., Buffalo, N.Y.) at various temperature, humidity, external tubing type, and tube length. (External tubing is the tubing between the oxygen concentrator and the cryogenic unit, e.g., Home-Away System by In-X Corp., Denver Colo.)

No External Tubing

| Ambient Temp. | Rel. Hum. | Dew Point | Moisture/Month |
|---|---|---|---|
| 84° F. | 71% | −41.6° C. | 4.70 g/month |
| 73° F. | 24% | −47.8° C. | 2.35 g/month |

With 30 Feet of Bev-A-Line Tubing

| Ambient Temp. | Rel. Hum. | Dew Point | Moisture/Month |
|---|---|---|---|
| 84° F. | 70% | −38.2° C. | 6.85 g/month |
| 75° F. | 24% | −46.0° C. | 2.90 g/month |

With 20 Feet of Bev-A-Line Tubing

| Ambient Temp. | Rel. Hum. | O2 Dew Point | Moisture/Month |
|---|---|---|---|
| 84° F. | 70% | −39.2° C. | 6.15 g/month |
| 75° F. | 24% | −47.4° C. | 2.45 g/month |

With 10 Feet of Bev-A-Line Tubing

| Ambient Temp. | Rel. Hum. | O2 Dew Point | Moisture/Month |
|---|---|---|---|
| 84° F. | 70% | −40.3° C. | 5.25 g/month |
| 73° F. | 24% | −47.6° C. | 2.42 g/month |

With 30 Feet of Vinyl Tubing

| Ambient Temp. | Rel. Hum. | Dew Point | Moisture/Month |
|---|---|---|---|
| 84° F. | 72% | −35.7° C. | 8.95 g/month |

With 20 Feet of Vinyl Tubing

| Ambient Temp. | Rel. Hum. | Dew Point | Moisture/Month |
|---|---|---|---|
| 84° F. | 71% | −37.0° C. | 7.85 g/month |

With 10 Feet of Vinyl Tubing

| Ambient Temp. | Rel. Hum. | Dew Point | Moisture/Month |
|---|---|---|---|
| 84° F. | 71% | −38.7° C. | 6.63 g/month |

Figure 8:
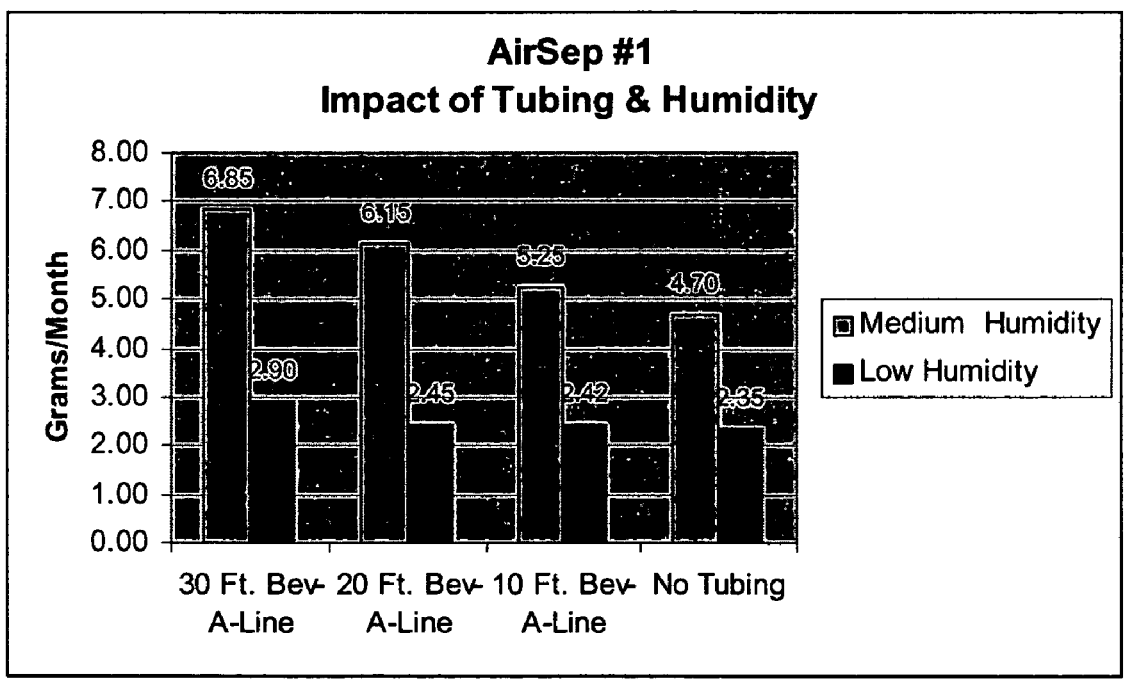
FIG. 8 is a bar graph showing the amount of moisture diffusion into the oxygen enriched feedstream relative to the length of an external tubing.

As shown in FIG. 8, an increased length of external tubing resulted in increased moisture in the oxygen enriched feedstream. At a low ambient temperature and humidity, the amount of moisture increase is relatively small. For example, the moisture content increased by only 0.55 g/month with 30 feet of tubing. At a higher ambient temperature and humidity, the 30 feet of tubing resulted in an additional 2.15 g/month of moisture. See FIG. 8. It should also be noted that under these conditions, the additional moisture in the oxygen enriched feedstream that was generated by the oxygen concentrator was 2.35 g/month. Thus, the total increase in moisture from both the concentrator and 30 feet of tubing resulting from the ambient temperature and humidity increase was 4.5 g/month.

Figure 9:
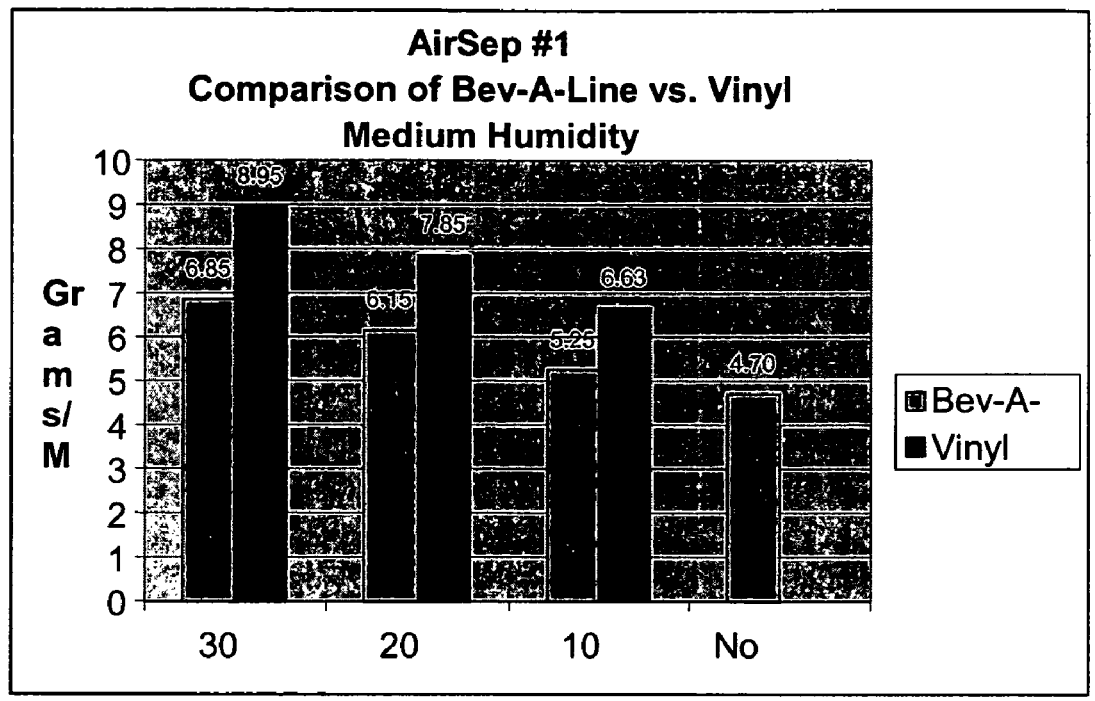
FIG. 9 is a bar graph showing a different amount of moisture diffusion through different tubing materialsat various tubing lengths.

As shown in FIG. 9, this example also further demonstrates that the Bev-A-Line tubing has a lower moisture permeability than a vinyl tubing.

Example 5

This example illustrates the moisture content of various oxygen enriched gas feedstreams that are generated using Puritan Bennett Oxygen Concentrator (Puritan-Bennett Corp., Pleasanton, Calif.) at various temperature, humidity, and external length of Bev-A-Line tubing.

With 30 Feet of Bev-A-Line Tubing

| Ambient Temp. | Rel. Hum. | Dew Point | Moisture/Month |
|---|---|---|---|
| 91° F. | 79% | −31.2° C. | 14.3 g/month |
| 84° F. | 61% | −35.8° C. | 8.90 g/month |
| 73° F. | 16% | −44.1° C. | 3.60 g/month |

With 20 Feet of Bev-A-Line Tubing

| Ambient Temp. | Rel. Hum. | Dew Point | Moisture/Month |
|---|---|---|---|
| 91° F. | 79% | −31.5° C. | 13.9 g/month |
| 86° F. | 59% | −36.4° C. | 8.35 g/month |
| 73° F. | 16% | −44.4° C. | 3.45 g/month |

With 10 Feet of Bev-A-Line Tubing

| Ambient Temp. | Rel. Hum. | Dew Point | Moisture/Month |
|---|---|---|---|
| 91° F. | 79% | −31.9° C. | 13.3 g/month |
| 86° F. | 61% | −36.8° C. | 7.95 g/month |
| 73° F. | 16% | −44.8° C. | 3.30 g/month |

With no External Tubing

| Ambient Temp. | Rel. Hum. | Dew Point | Moisture/Month |
|---|---|---|---|
| 90° F. | 78% | −32.1° C. | 13.0 g/month |
| 88° F. | 58% | −36.7° C. | 8.10 g/month |
| 75° F. | 15% | −44.9° C. | 3.28 g/month |

Figure 10:
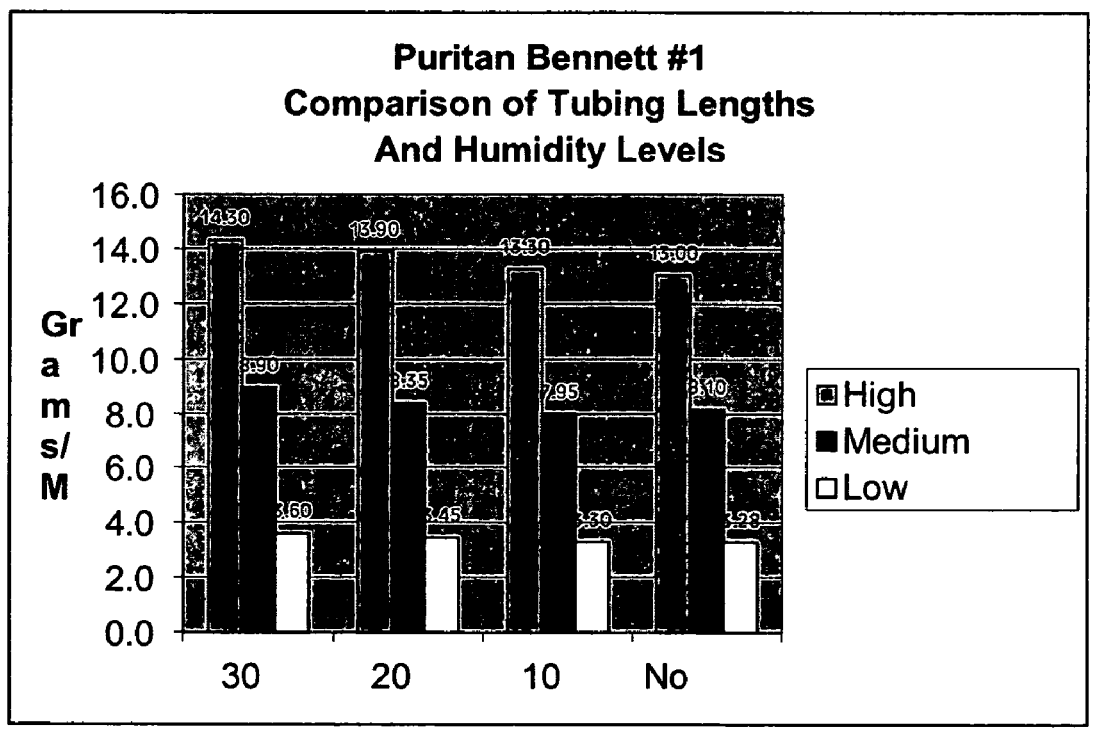
FIG. 10 is a bar graph showing different rates of moisture diffusion at various ambient humidity levels.

As shown in FIG. 10, a relatively little additional moisture diffuses into the device through the Bev-A-Line tubing. For example, using 30 feet of external Bev-A-Line tubing, at a relatively low humidity level about 0.32 g/month of additional moisture is introduced into the cryogenic unit. At a medium humidity level under the same conditions, about 0.80 g/month of additional moisture is introduced into the cryogenic unit. And under the same conditions at a high humidity level, about 1.3 g/month of additional moisture is introduced into the cryogenic unit. As the data shows, the moisture content in the oxygen enriched feedstream was affected more by the relative humidity level than the tubing length. For example, in the absence of any external tubing, the moisture level in the oxygen enriched feedstream generated by the oxygen concentrator was 9.72 g/month higher at a high humidity condition compared to a low humidity condition.

Example 6

This example tests the moisture content in the oxygen enriched gas feedstream produced by different oxygen concentrators.

Figure 11:
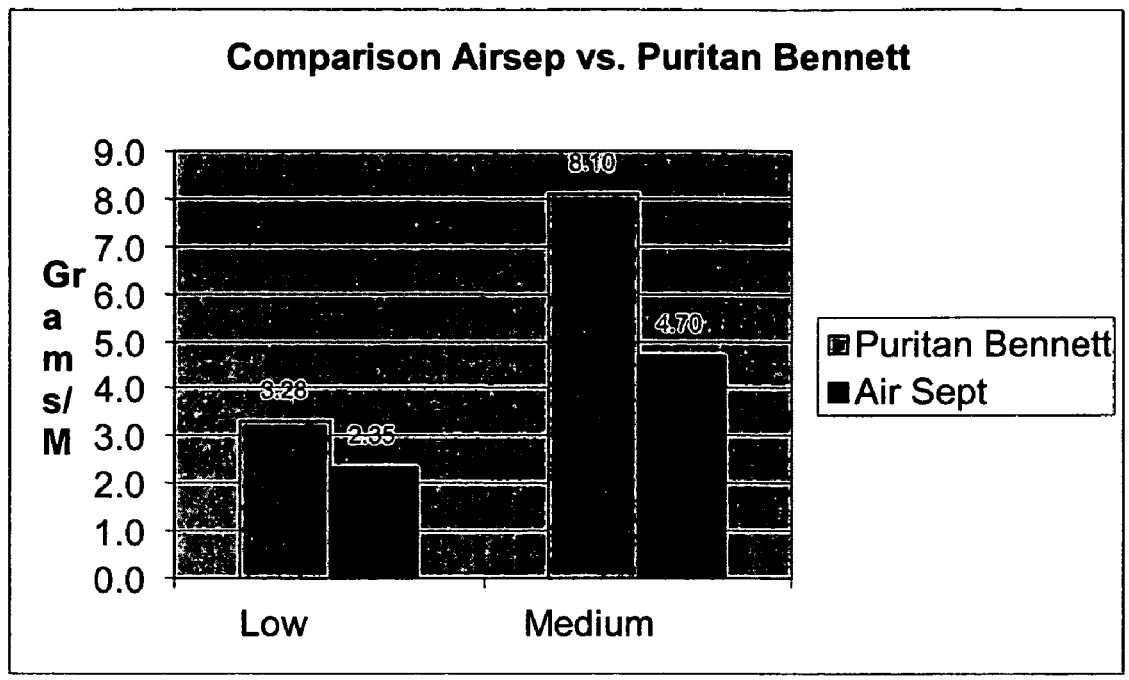
FIG. 11 is a bar graph showing the difference in the amount of moisture present in an oxygen enriched gas feedstream produced by AirSep Oxygen Concentrator and Puritan Bennett Oxygen Concentrator.

The amount of moisture in the oxygen enriched gas feedstreams produced by two different oxygen concentrators were measured. As shown in FIG. 11, the oxygen enriched gas feedstream produced by AirSep Concentrator (AirSep Corp., Buffalo, N.Y.) had a lower moisture content than the oxygen enriched gas feedstream produced by Puritan Bennett Concentrator (Puritan-Bennett Corp., Pleasanton, Calif.). Moreover, an increase in the ambient humidity level resulted in a smaller increase in moisture in the oxygen enriched gas feedstream produced by the AirSep model.

Example 7

This example compares the moisture content in the oxygen enriched gas feedstream produced by Puritan Bennett #1 Oxygen Concentrator (Puritan-Bennett Corp. Pleasanton, Calif.) at different places.

The moisture content in the oxygen enriched gas feedstream produced by Puritan Bennett #1 Oxygen Concentrator is measured at the Concentrator's outlet (after the internal tubing) and at the gas separation sieve bed outlet (prior to the internal tubing).

| Ambient Temp. | Rel. Hum. | Dew Point | Moisture/Month |
|---|---|---|---|
| 88° F. | 78% | −56.2° C. | 0.87 g/month |
| 89° F. | 61% | −58.4° C. | 0.65 g/month |
| 68° F. | 24% | −61.7° C. | 0.47 g/month |

Figure 12:
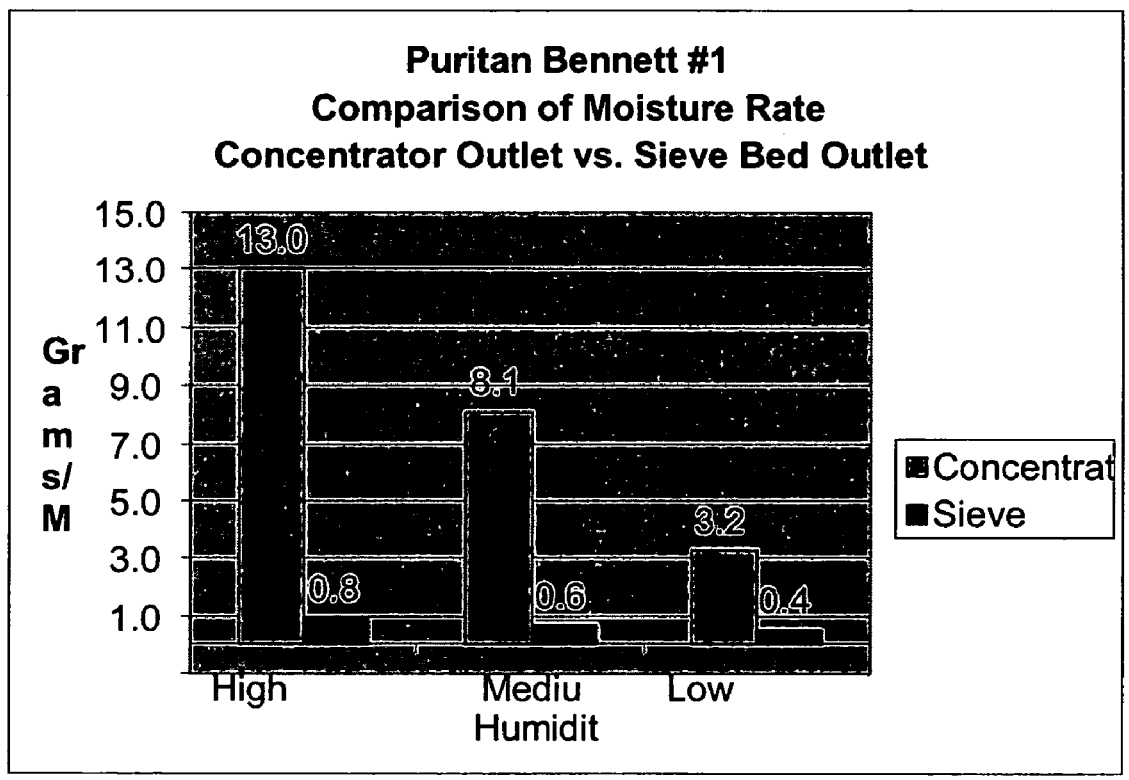
FIG. 12 is a bar graph showing the moisture content of an oxygen enriched gas feedstream at the oxygen gas separation sieve bed outlet and the oxygen conentrator unit outlet of Puritan Bennett #1 Oxygen Concentrator.

As shown in FIG. 12, this test indicates that most of the moisture in the oxygen enriched gas feedstream is due to diffusion of moisture into the gas feedstream through the internal tubing. Even at a high temperature and humidity, only a very little moisture is present in the oxygen enriched gas feedstream at the gas separation sieve bed outlet.

Example 8

This example shows the effect of a gas flow rate on the moisture level in an oxygen enriched gas feedstream using Puritan Bennett #1 oxygen concentrator with 30 feet of Bev-A-Line external tubing.

Figure 13:
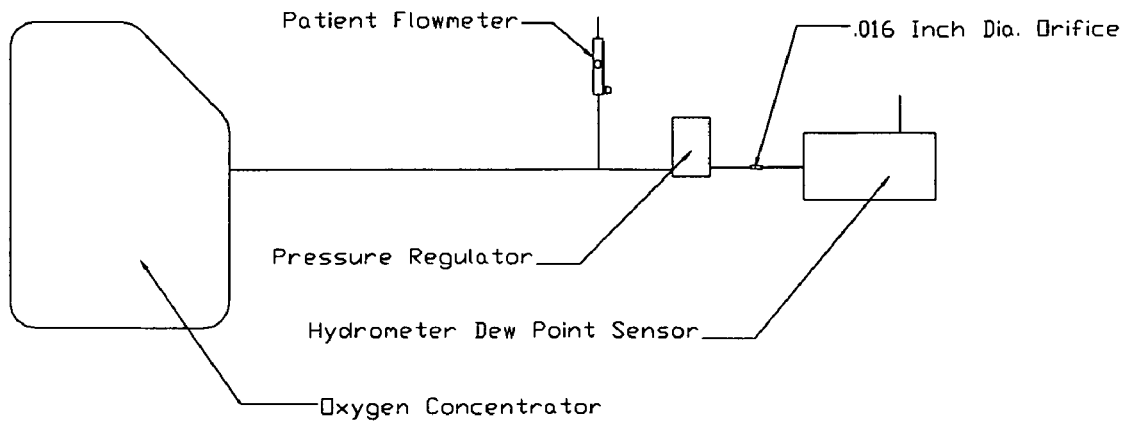
FIG. 13 is a schematic illustration of the apparatus set up that is used in Example 8.
Figure 14:
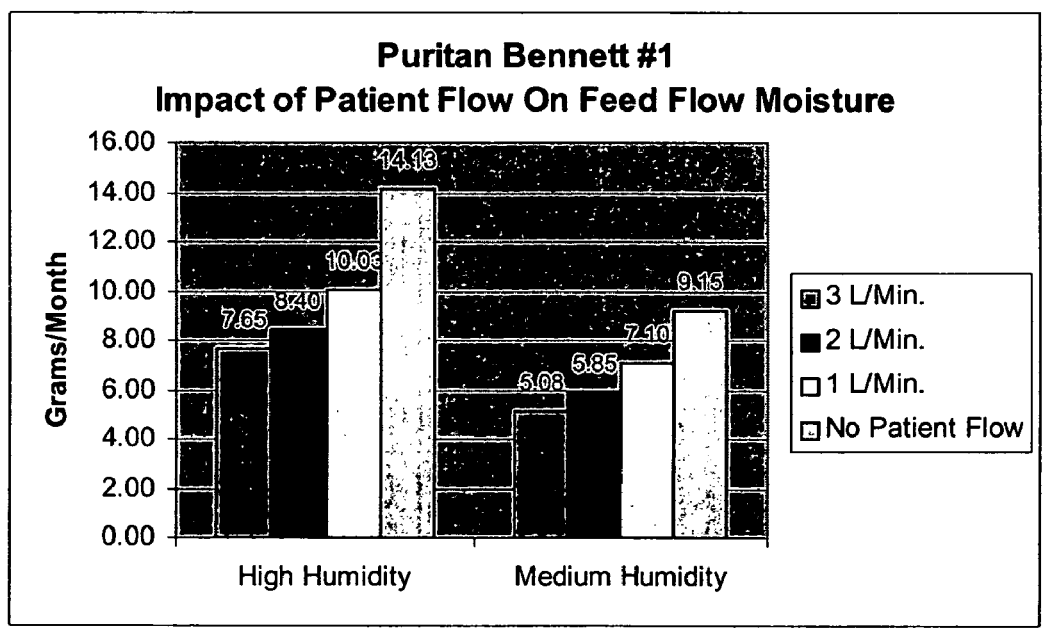
FIG. 14 is a bar graph showing the moisture content of the oxygen enriched gas feedstream at various output rates of an oxygen gas concentrator device.

Examples 2-7 above utilized the oxygen concentrator flow rate of about 1.1 L/min with the entire gas flow going directly to the cryogenic unit. This is equivalent to using the oxygen concentrator and the cryogenic unit without diverting any oxygen enriched gas feedstream to a patient. In this example, the apparatus was configured as schematically shown in FIG. 13. The gas feedstream flow rate was set such that its flow rate to the cryogenic unit was maintained at about 1.1 L/min. A T-joint allowed some of the oxygen enriched gas feedstream to be diverted to a patient. Diversion of the oxygen enriched gas feedstream to a patient was achieved while still maintaining the flow rate of the oxygen enriched gas feedstream to the cryogenic unit at about 1.1 L/min. When some of the gas feedstream was diverted to the patient (up to 3 L/min. in some cases), the flow rate through the oxygen concentrator device was increased correspondingly to maintain the flow rate of the gas feedstream to the cryogenic unit at about 1.1 L/min. As shown in FIG. 14, this increased oxygen concentrator output rate effectively reduced the moisture content of the oxygen enriched gas feedstream flowing into the cryogenic unit.

The Flow Rate of 3 L/min to the Patient

| Ambient Temp. | Rel. Hum. | Dew Point | Moisture/Month |
|---|---|---|---|
| 91° F. | 81% | −37.2° C. | 7.65 g/month |
| 86° F. | 59% | −41.0° C. | 5.08 g/month |

The Flow Rate of 2 L/min to the Patient

| Ambient Temp. | Rel. Hum. | Dew Point | Moisture/Month |
|---|---|---|---|
| 91° F. | 82% | −36.3° C. | 8.40 g/month |
| 87° F. | 61% | −39.7° C. | 5.85 g/month |

The Flow Rate of 1 L/min to the Patient

| Ambient Temp. | Rel. Hum. | Dew Point | Moisture/Month |
|---|---|---|---|
| 91° F. | 82% | −34.6° C. | 10.03 g/month |
| 88° F. | 64% | −37.9° C. | 7.10 g/month |

No Flow to the Patient

| Ambient Temp. | Rel. Hum. | O2 Dew Point | Moisture/Month |
|---|---|---|---|
| 91° F. | 81% | −31.3° C. | 14.13 g/month |
| 88° F. | 61% | −35.5° C. | 9.15 g/month |

As shown in data above, at 85° F. ambient temperature and 60% relative humidity, the oxygen enriched gas feedstream at 2 L/min flow rate to the patient resulted in effectively 36% less moisture content compared to no diversion of the oxygen enriched gas feedstream to the patient.

Example 9

This test shows the moisture level in an oxygen enriched gas feedstream that is produced within an initial few hours of operating an oxygen concentrator that had been shut down for an extended period of time.

Puritan Bennett #1 Oxygen Concentrator was turned off and stored at 75° F. and 18% relative humidity conditions for several months. The flow rate of the oxygen concentrator was set to 1.1 L/min., and the moisture content of the oxygen enriched gas feedstream generated by the device on start-up was measured without the use of any external tubing.

| Unit Run Time (Hour:Min) | Dew Point (° C.) | Moisture/Month (grams/month) |
|---|---|---|
| 00:01 | −14.5 | 69.2 |
| 00:05 | −18.8 | 46.5 |
| 00:10 | −22.2 | 34.1 |
| 00:15 | −23.2 | 30.9 |
| 00:20 | −23.9 | 29.2 |
| 00:25 | −24.5 | 27.5 |
| 00:30 | −24.9 | 26.5 |
| 00:45 | −25.9 | 23.8 |
| 01:00 | −26.6 | 22.2 |
| 01:15 | −27.2 | 21.1 |
| 01:30 | −27.7 | 20.0 |
| 02:00 | −28.5 | 18.5 |
| 02:30 | −29.3 | 17.2 |
| 04:15 | −31.9 | 13.3 |
| 05:15 | −33.3 | 11.5 |
| 06:15 | −34.2 | 10.5 |
| 07:15 | −35.3 | 9.38 |
| 26:00 | −41.8 | 4.62 |
| 50:00 | −43.5 | 3.85 |
| 74:00 | −43.1 | 4.03 |

Figure 15:
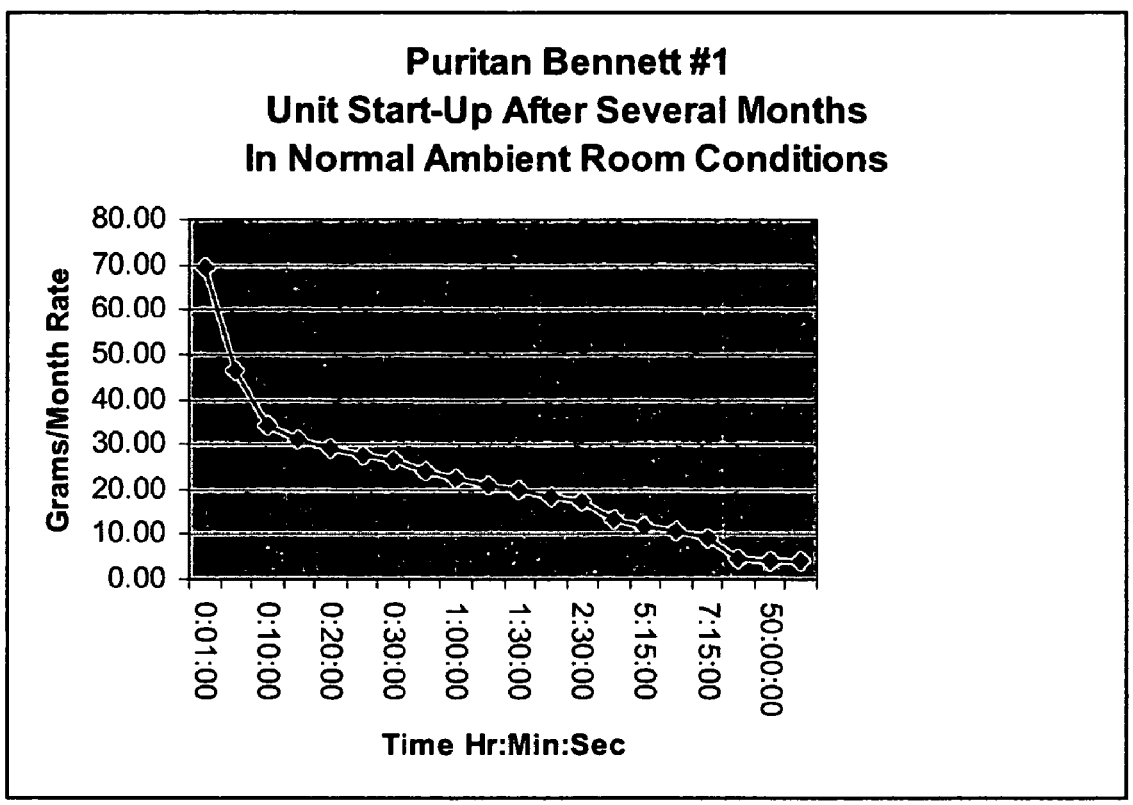
FIG. 15 is a graph showing the moisture level in an oxygen enriched gas feedstream that is produced within an initial few hours of operating an oxygen concentrator that had been shut down for an extended period of time.

As shown in data above and FIG. 15, the additional moisture measured in the oxygen enriched gas feedstream in the first 50 hours was about 0.22 grams. It appears that an oxygen concentrator absorbs some moisture in its sieve beds even when the device is not used. During the initial few hours of its operation, there is an elevated moisture level in the initial oxygen enriched gas feedstream.

Calculations:
To determine the moisture content in grams/month
    Read dew point temperature from hydrometer
    Convert degree centigrade to degree Fahrenheit Look up moisture content of saturated air on FIG. 16
Convert from grains/ft³ to grams/month based on a 1.1 liter/minute flow for 30 days
For example:
Dew Point −36.1° C.=−33° F.
At −33° F. there is 0.0790 grains/ft³
To convert there is 0.0353 ft³/L and 0.0648 g/grain
Therefore (0.0790 grains/ft³)(0.0353ft³/L)(0.0648 g/grain)=0.000181 g/L
(0.000181 g/L)(1.1 L/min.)(1440 min./day)(30 days/mo.)= 8.60 g/month.

To determine the additional moisture from starting up an oxygen concentrator that has not been used for an extended time.
For each time interval convert degree centigrade to degree Fahrenheit
Look up moisture content of saturated air on attached chart
Calculate total moisture content over interval in grams (note for all but the last two intervals I used the starting dew point, but for the last two I used an average dew point due to the length of those intervals.)
Add up moisture over all intervals
Subtract normal moisture over time period.
For example:

−14.5° C.=6° F. which has 0.637 grains/ft³

(0.637 grains/ft³)(0.0353ft³/L)(0.0648 g/grain)(1.1 L/min.)(5 min)=0.0080 g

Using the similar calculations:

(0.4272 grains/ft³)(0.0353ft³/L)(0.0648 g/grain)(1.1 L/min.)(5 min)=0.0054 g (0.3141 grains/ft³)(0.0353ft³/L)(0.0648 g/grain)(1.1 L/min.)(5 min)=0.0040 g (0.2829 grains/ft³)(0.0353ft³/L)(0.0648 g/grain)(1.1 L/min.)(5 min)=0.0036 g (0.2683 grains/ft³)(0.0353ft³/L)(0.0648 g/grain)(1.1 L/min.)(5 min)=0.0034 g (0.2546 grains/ft³)(0.0353ft³/L)(0.0648 g/grain)(1.1 L/min.)(5 min)=0.00321 g (0.2413 grains/ft³)(0.0353ft³/L)(0.0648 g/grain)(1.1 L/min.)(15 min)=0.0091 g (0.2230 grains/ft³)(0.0353ft³/L)(0.0648 g/grain)(1.1 L/min.)(15 min)=0.0084 g (0.2054 grains/ft³)(0.0353ft³/L)(0.0648 g/grain)(1.1 L/min.)(15 min)=0.0078 g (0.1946 grains/ft³)(0.0353ft³/L)(0.0648 g/grain)(1.1 L/min.)(15 min)=0.0074 g (0.1842 grains/ft³)(0.0353ft³/L)(0.0648 g/grain)(1.1 L/min.)(30 min)=0.0140 g (0.1700 grains/ft³)(0.0353ft³/L)(0.0648 g/grain)(1.1 L/min.)(30 min)=0.0128 g (0.1530 grains/ft³)(0.0353ft³/L)(0.0648 g/grain)(1.1 L/min.)(105 min)=0.0404 g (0.1210 grains/ft³)(0.0353ft³/L)(0.0648 g/grain)(1.1 L/min.)(60 min)=0.0183 g (0.1055 grains/ft³)(0.0353ft³/L)(0.0648 g/grain)(1.1 L/min.)(60 min)=0.0160 g (0.0965 grains/ft³)(0.0353ft³/L)(0.0648 g/grain)(1.1 L/min.)(60 min)=0.0146 g (0.0600 grains/ft³)(0.0353ft³/L)(0.0648 g/grain)(1.1 L/min.)(1125 min)=0.1701 g (0.0390 grains/ft³)(0.0353ft³/L)(0.0648 g/grain)(1.1 L/min.)(1440 min)=0.1415 g 3000 min 0.489 g Normal Moisture (0.0350 grains/ft³)(0.0353ft³/L)(0.0648 g/grain)(1.1 L/min.)(3000 min)=0.267 g Additional Moisture 0.489 g−0.267 g=0.222 g The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A portable gas liquefaction system comprising:
    a compressor receiving a supply of gas and adapted to provide a supply of compressed gas from the supply of gas;
    a separator operatively coupled to the compressor to receive the supply of compressed gas, wherein the separator is adapted to provide a supply of oxygen enriched gas from the supply of compressed gas;
    a desiccant cartridge assembly configured and arranged so as to receive the supply of oxygen enriched gas from the separator, wherein the desiccant cartridge assembly is adapted to remove moisture from the supply of oxygen enriched gas to produce a supply of dehumidified oxygen enriched gas; and
    a liquefaction system configured and arranged so at to receive the supply of dehumidified oxygen enriched gas, wherein the liquefaction system is adapted to produce a supply of liquefied oxygen from the supply of dehumidified oxygen enriched gas.

2. The system of claim 1, wherein the desiccant cartridge assembly is removably coupled in a gas flow path between the separator and the liquefaction system.

3. The system of claim 1, wherein the separator comprises a plurality of sieve beds.

4. The system of claim 3, further comprising a product tank adapted to receive the supply of oxygen enriched gas from the separator, and wherein the desiccant cartridge assembly is disposed in a gas flow path between the product tank and the liquefaction system.

5. The system of claim 1, further comprising a dewar adapted to receive and store the liquefied oxygen from the liquefaction system.

6. The system of claim 1, wherein the desiccant cartridge assembly comprises a housing, and a desiccant material disposed in the housing.

7. The system of claim 1, wherein the desiccant material comprises zeolite, silica gel, activated alumina, activated clay, activated carbon, activated charcoal, or a combination thereof.

8. The system of claim 6, further comprising an indicator adapted to indicate an amount of moisture present in the desiccant material.

9. The system of claim 1, further comprising an outlet port operatively coupled to an outlet of the separator, wherein the outlet port is adapted to provide at least a portion the oxygen enriched gas to a patient.

10. The system of claim 1, wherein liquefaction system comprises a cryocooler adapted to cool the dehumidified oxygen enriched gas.

11. A portable gas liquefaction system comprising: compressing means for generating a supply of compressed gas from a supply of gas; separating means for providing a supply of oxygen enriched gas from the supply of compressed gas;
dehumidifying means for receiving and removing moisture from the supply of oxygen enriched gas to produce a supply of dehumidified oxygen enriched gas; and liquefying means for producing a supply of liquefied oxygen from the supply of dehumidified oxygen enriched gas, wherein the dehumidifying means is a desiccant cartridge assembly adapted to be removably coupled in a gas flow path between the separating means and the liquefying means.

12. The system of claim 11, further comprising gas storing means for storing the oxygen enriched gas from the separator, and wherein the dehumidifying means is disposed in a gas flow path between the storing means and the liquefying means.

13. The system of claim 11, further comprising liquefied oxygen storing means for storing the liquefied oxygen from the liquefying means.

14. The system of claim 11, further comprising moisture monitoring means for monitoring an amount of moisture present in the dehumidifying means.

15. The system of claim 11, further coupling means for providing at least a portion of the oxygen enriched gas from the separating means to a patient.

16. A method of providing liquefied oxygen, comprising:
compressing a supply of gas to product a supply of compressed gas;
generating a supply of oxygen enriched gas from the supply of compressed gas;
providing the supply of oxygen enriched gas to a desiccant cartridge assembly;
dehumidifying the supply of oxygen enriched in the desiccant cartridge assembly to produce a supply of dehumidified oxygen enriched gas; and
providing the supply of dehumidified oxygen enriched gas to a liquefaction system;
producing a supply of liquefied oxygen from the supply of dehumidified oxygen enriched gas using the liquefaction system.

17. The method of claim 16, further comprising periodically replacing the desiccant cartridge assembly.

18. The method of claim 16, further comprising storing the oxygen enriched is a storage assembly.

19. The method of claim 16, further comprising storing the liquefied oxygen in a dewar.

20. The method of claim 16, further comprising monitoring an amount of moisture present in the desiccant cartridge assembly.

21. The method of claim 16, further coupling providing at least a portion of the oxygen enriched gas to an outlet port for delivery to a patient.

* * * * *